United States Patent
Geelhoed et al.

(10) Patent No.: US 6,599,017 B2
(45) Date of Patent: Jul. 29, 2003

(54) MEDICAL C-ARM DEVICE PROVIDED WITH REINFORCED RUNNING SURFACES

(75) Inventors: Frans Eduard Nicolaas Geelhoed, Eindhoven (NL); Hendrik Wijbe Johannes De Vries, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 36 days.

(21) Appl. No.: 10/076,353

(22) Filed: Feb. 15, 2002

(65) Prior Publication Data
US 2002/0126801 A1 Sep. 12, 2002

(30) Foreign Application Priority Data
Feb. 19, 2001 (EP) ............................................. 01200578

(51) Int. Cl.[7] ............................................. F16C 29/04
(52) U.S. Cl. .......................................................... 384/58
(58) Field of Search ............................... 384/58, 52, 55, 384/59, 57

(56) References Cited

U.S. PATENT DOCUMENTS 4,722,150 A * 2/1988 Jacobs et al. .................. 384/50
6,347,887 B1 * 2/2002 Bolzonaro et al. ............ 384/58

FOREIGN PATENT DOCUMENTS

DE          29802014       6/1998      ............ A61B/6/02

* cited by examiner

*Primary Examiner*—Lenard A. Footland
(74) *Attorney, Agent, or Firm*—John Vodopia

(57) ABSTRACT

A device that is provided with a C-arm 2 for carrying medical devices 5, 6, which C-arm is attached to a carrier 3 so as to be adjustable along its circumference, which carrier is provided with a bearing block 7 that is provided on both sides with at least one row of roller elements 8. The C-arm is hollow and is provided on both sides with at least two oppositely situated internal running surfaces 9 for the roller elements. The device is characterized in accordance with the invention in that the running surfaces are provided with reinforcement elements 11. The invention also relates to a bearing block as described as part of the device in accordance with the invention.

10 Claims, 1 Drawing Sheet

MEDICAL C-ARM DEVICE PROVIDED WITH REINFORCED RUNNING SURFACES

Figure 1:
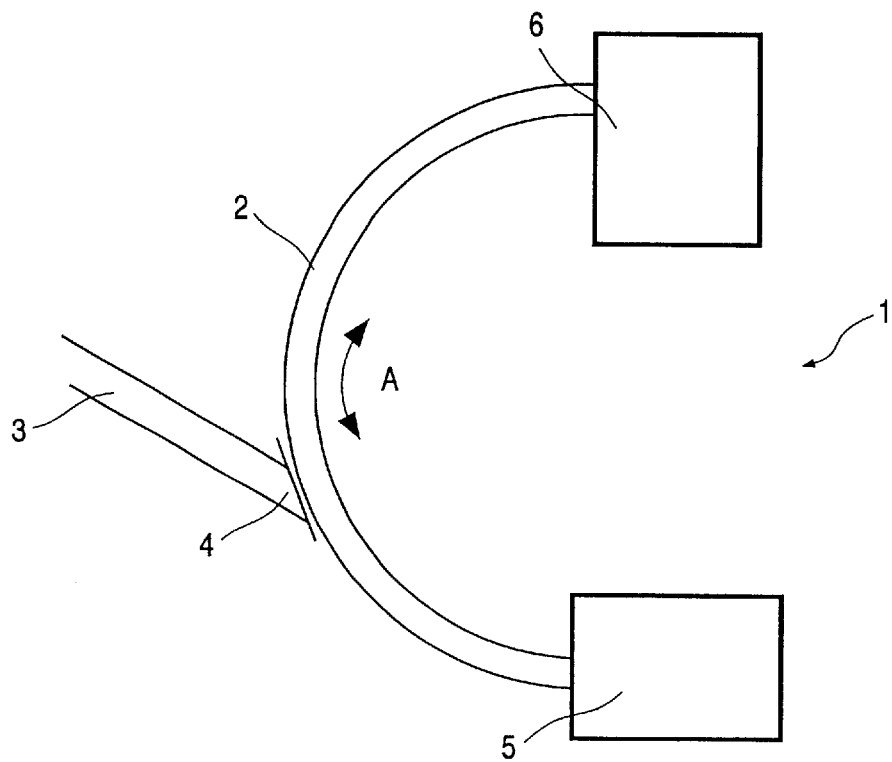

The present invention relates to a device that is provided with a C-arm for the mounting of medical equipment, which C-arm is attached to a carrier so as to be adjustable along its circumference, said carrier being provided with a bearing block that is provided with at least one row of roller elements on both sides, the C-arm being constructed so as to be hollow and being provided on both sides with at least two oppositely situated internal running surfaces for the roller elements.

Devices of this kind set forth are used in practice for medical examination of a patient. To this end, an emitter of, for example, X-rays is attached to one end of the C-arm whereas a corresponding receiver is attached to the opposite end. The C-arm is adjustable inter alia along its circumference and hence can be accurately positioned relative to the patient who is accommodated on a table, for example, during a surgical intervention.

In order to ensure safe operation in all circumstances, the design of a device of this kind should satisfy a number of design requirements that are contradictory in some cases. First of all, the beam from the emitter to the receiver should remain within predetermined boundaries in all circumstances. This means that the C-arm should have a high bending strength. Furthermore, the construction of the device should be as light as possible so as to achieve an as high as possible degree of moeuvrability. This is of importance, for example, for the displacement of the device and for the adjustment of the C-arm that can be performed manually as well as with the aid of a motor. Furthermore, the device should be capable of withstanding large temperature differences that may occur, for example, during transport. In order to satisfy the above requirements, the operation of the bearing for the C-arm should be smooth and light with a minimum amount of play.

A device of the kind set forth is known from DE 298 02 014. The cited document describes a device for medical diagnostic applications that is provided with a C-arm on which a radiation source is mounted at one side while a corresponding receiver is mounted at another side. The C-arm is journaled on a carrier. The bearing block is provided on both sides with two rows of wheels that are situated one above the other. The C-arm is constructed so as to be hollow and is provided with internal running surfaces for the wheels. The running surfaces are provided with guide rails that have a semi-circular cross-section. The wheels are provided with corresponding recesses. This construction minimizes the play in the lateral direction and prevents the C-arm from performing undesirable lateral pivotal motions during its movement along its circumference.

The known device has the drawback that the guide rails must be attached to the C-arm with a bias, for example, by means of a construction involving tension springs and compression springs. A construction of this kind has a negative effect on inter alia the weight of the C-arm and it also disturbs the delicate balance between weight and bending strength that is realized under the influence of the design requirements imposed on the C-arm.

The object of the invention is different, that is, it aims to provide a device of the kind set forth that offers a higher mechanical loadability of the bearing surfaces in combination with a low weight and a high bending strength.

To achieve this, the device in accordance with the invention is characterized in that the running surfaces are provided with reinforcement elements.

The running surfaces thus reinforced are suitable for co-operation with a bearing block that is provided with reinforced roller elements. Because reinforced roller elements are capable of taking up a higher load, the number of roller elements in each row can be advantageously reduced. This results in a shorter bearing block which in its turn enables a larger angulation angle for the C-arm.

The reinforcement elements in a first preferred embodiment of the device in accordance with the invention are strip-shaped. Choosing a shape in the form of a strip offers several advantages. The additional weight of the reinforcement elements is thus minimized minimum, so that the delicate balance between weight and bending strength for the C-arm is hardly disturbed. Moreover, the strips expand mainly in the longitudinal direction under the influence of temperature fluctuations. This expansion can be simply taken up by allowing some play in the longitudinal direction.

The running surfaces in a practical preferred embodiment are provided with recesses for receiving the reinforcement elements. The reinforcement elements can thus be quickly and efficiently fitted in the correct position on the running surfaces.

The recesses in an elegant preferred embodiment are form-locking. The reinforcement elements are preferably arranged loosely in the recesses. Bias constructions of the kind described above in relation to the guide elements of the known device can thus be dispensed with. Moreover, any expansion and contraction of the reinforcement elements due to temperature fluctuations can be taken up without special steps being required.

The reinforcement elements preferably contain a metal such as hardened steel. The roller elements may be reinforced by using a hardened metal. As a result of the use of the reinforcement elements, the C-arm may contain aluminum or a composite material in known manner. Thanks to the use of the metal reinforcement elements, such a softer material is effectively protected against damaging by the reinforced roller elements during use.

Each row of the bearing block in another preferred embodiment comprises no more than six roller elements. This advantageous reduction of the number of roller elements is possible because of the use of the reinforced roller elements that are individually capable of withstanding a higher load.

The invention also relates to a bearing block as described as part of the device in accordance with the invention.

Figure 2:
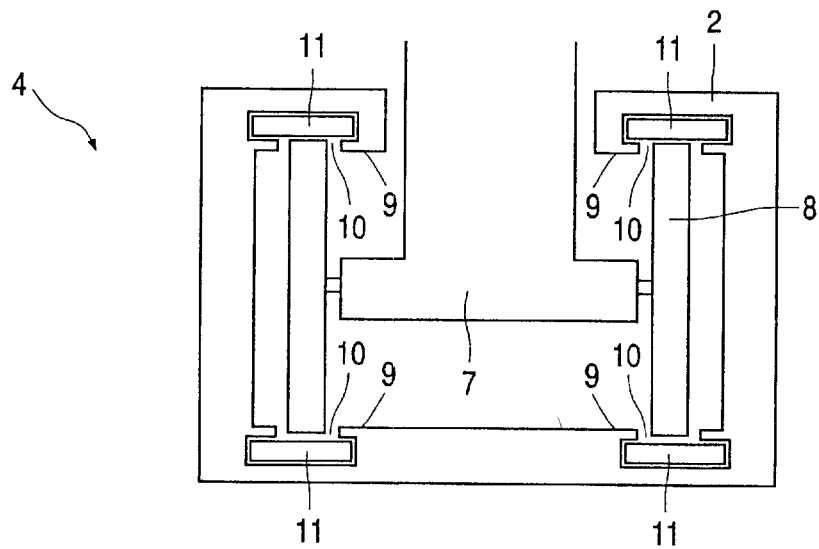

The invention will be described in detail hereinafter with reference to the drawings; therein:

FIG. 1 is a diagrammatic view of a device for medical applications in which the invention is used, and FIG. 2 is a diagrammatic cross-sectional view taken at the area of the bearing in FIG. 1.

FIG. 1 shows a device 1 for medical applications in which the invention is used. The device 1 is a so-called medical C-arm system. The C-arm 2 is attached to a carrier 3 by way of a bearing 4. Medical equipment is attached to both ends of the C-arm 2. In the present example the device 1 is an X-ray system that includes an X-ray source or emitter 5 and an oppositely situated image intensifier or receiver 6.

In practice the device 1 is used for performing examinations on a patient. The device 1 may be constructed so as to be mobile; to this end, it is moeuvered in such a manner that the patient is positioned between the X-ray source 5 and the associated image receiver 6 during the examination. Various adjustment facilities are provided for adjusting the C-arm to the correct position. The C-arm 2 is movable inter alia along its circumference as indicated by way of the arrow A.

FIG. 2 is a diagrammatic cross-sectional view taken at the area of the bearing 4 in FIG. 1. This Figure clearly shows that the C-arm 2 is constructed so as to be hollow and that it has a generally U-shaped cross-section; on both sides thereof there are provided oppositely situated internal running surfaces 9. The bearing block 7 is provided with one row of roller elements 8 on both sides.

As is well known in this technical field, the distance between the oppositely situated running surfaces 9 is slightly larger than the diameter of the roller elements (also referred to as runners or wheels), so that the roller elements 8 will always be in contact with one of the running surfaces 9 during the movement of the C-arm. It is to be noted that in the context of the present invention the term "running surface" is to be understood to mean that part of the internal surface of the C-arm that can make contact with the roller elements.

Each of the running surfaces 9 is provided with a recess 10 in which a reinforcement element 11 is accommodated. The reinforcement elements 11 in general are strip-shaped and preferably cover essentially the entire surface area of the running surfaces 10. The reinforcement elements 11 follow the shape of the running surfaces and hence the shape of the C-arm 2.

The recesses 10 are preferably form-locking, so that reinforcement elements 111 can be loosely arranged therein. Consequently, additional aids, such as glue or spring constructions as used for the guide elements in conformity with the state of the art, can now be dispensed with.

The material of the reinforcement elements is preferably metal. The metal may be hardened. Hardened steel is an example of a material that is suitable in this respect.

As is customary in this technical field, the material of the C-arm is, for example, aluminum or a composite material. The use of the reinforcement elements in accordance with the invention makes it possible to choose a type of material for the wheels that is stronger than customarily used thus far, that is, for example, the previously mentioned hardened steel.

The reinforcement elements prevent damaging of the softer material of the running surfaces that would otherwise occur, for example due to "scoring" of the wheels. Thanks to the use of the stronger material, the wheels can individually withstand a higher mechanical load and the number of wheels in each row can be advantageously reduced.

The number of wheels in each row can be adapted to the relevant circumstances. This number is dependent inter alia on the diameter of the wheels. Preferably, the number of wheels in each row amounts to eight or even less, for example, a number between two and seven. This reduction of the number of wheels offers the important advantage of an increased angulation angle of the C-arm. This is because the dimensions of the bearing block 7 are determined by the number of wheels in each row. A reduction of the number of wheels, consequently, directly leads to a shorter bearing block. The length of the bearing block in its turn co-determines the angulation angle of the C-arm 2. A reduction of the length of the bearing block thus results directly in an increase of the angulation angle, which increase is expected to be of the order of magnitude of some tens of degrees.

On the other hand, the reinforcement elements make the C-arm itself stronger; this may create possibilities for the use of less strong materials for the various components.

Preferably, the dimensions of the recesses 10 are slightly larger than the dimensions of the strips 11. Fluctuations in the ambient temperature can thus be simply taken up, despite the differences in the coefficient of expansion of the material of the C-arm 2 and that of the material of the strips 11.

As is known in this technical field, so-called side roller elements (not shown) are also attached to the bearing block 7. The side roller elements run on further internal running surfaces (not shown) and serve to prevent undesirable lateral movement of the C-arm 2.

The invention, of course, is not restricted to the preferred embodiment shown and described above. The invention can be used, for example, for all medical C-arm devices that are known in this technical field, that is, devices provided with a fixed bearing block as well as those provided with a movable bearing block and with one or with two rows of wheels on both sides of the bearing block.

After having read the present document, a person skilled in the art of the present technical field will have no problem in conceiving alternative embodiments in which the idea of the invention is implemented. Therefore, the invention in general covers any implementation that is within the scope of the appended claims, considered in conjunction with the foregoing description and the accompanying drawings.

What is claimed is:

1. A device that is provided with a C-arm (2) for the mounting of medical equipment (5, 6), which C-arm is attached to a carrier (3) so as to be adjustable along its circumference, said carrier being provided with a bearing block (7) that is provided with at least one row of roller elements (8) on both sides, the C-arm being constructed so as to be hollow and being provided on both sides with at least two oppositely situated internal running surfaces (9) for the roller elements, characterized in that the running surfaces are provided with reinforcement elements (11).

2. A device as claimed in claim 1, in which the reinforcement elements are strip-shaped.

3. A device as claimed in claim 1, in which the running surfaces are provided with recesses for receiving the reinforcement elements.

4. A device as claimed in claim 3, in which the recesses are form-locking.

5. A device as claimed in claim 4, in which the reinforcing elements are arranged loosely in the recesses.

6. A device as claimed in claim 1, in which the reinforcement elements contain a metal.

7. A device as claimed in claim 6, in which the reinforcement elements contain hardened steel.

8. A device as claimed in claim 1, in which the roller elements contain a hardened metal.

9. A device as claimed in claim 1, in which each row of the bearing block comprises no more than six roller elements.

10. A bearing block as described as part of the device as claimed in claim 1.

* * * * *